United States Patent
Chi et al.

(10) Patent No.: US 10,832,492 B2
(45) Date of Patent: Nov. 10, 2020

(54) PANORAMIC VISUALIZATION OF CORONARY ARTERIAL TREE

(71) Applicants: AGENCY FOR SCIENCE, TECHNOLOGY AND RESEARCH, Singapore (SG); SINGAPORE HEALTH SERVICES PTE LTD, Singapore (SG)

(72) Inventors: Yanling Chi, Singapore (SG); Liang Zhong, Singapore (SG); Ru San Tan, Singapore (SG); Weimin Huang, Singapore (SG); Jiayin Zhou, Singapore (SG); Kyaw Kyar Toe, Singapore (SG)

(73) Assignees: AGENCY FOR SCIENCE, TECHNOLOGY AND RESEARCH, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 116 days.

(21) Appl. No.: 16/090,181

(22) PCT Filed: Mar. 31, 2017

(86) PCT No.: PCT/SG2017/050185
§ 371 (c)(1),
(2) Date: Sep. 28, 2018

(87) PCT Pub. No.: WO2017/171656
PCT Pub. Date: Oct. 5, 2017

(65) Prior Publication Data
US 2019/0122445 A1 Apr. 25, 2019

(30) Foreign Application Priority Data
Mar. 31, 2016 (SG) .............................. 10201602544S

(51) Int. Cl.
*G06T 19/20* (2011.01)
*G06T 15/08* (2011.01)
(Continued)

(52) U.S. Cl.
CPC .............. *G06T 19/20* (2013.01); *A61B 6/032* (2013.01); *A61B 6/466* (2013.01); *A61B 6/504* (2013.01);
(Continued)

(58) Field of Classification Search
CPC .... G06T 11/40; G06T 11/00; G06T 2211/404; G06T 2207/30101; G06T 3307/30048;
(Continued)

(56) References Cited

U.S. PATENT DOCUMENTS

2009/0129641 A1* 5/2009 Zhou ...................... G06T 19/00
382/128
2009/0174712 A1* 7/2009 De Bliek ................ G06T 5/009
345/424

(Continued)

OTHER PUBLICATIONS

Wang, Chunliang, et al. "Can segmented 3D images be used for stenosis evaluation in coronary CT angiography?." Acta Radiologica 53.8 (2012): 845-851. (Year: 2012).*

(Continued)

*Primary Examiner* — Geoffrey E Summers
(74) *Attorney, Agent, or Firm* — Womble Bond Dickinson (US) LLP

(57) ABSTRACT

The present disclosure generally relates to an automated method and system for generating a panoramic visualization of a coronary arterial tree of a subject. The method comprises: acquiring an image volume of a thoracic cavity of the subject, the image volume providing a three-dimensional (3D) representation of the thoracic cavity; isolating a coronary structure in the 3D representation by abating one or (Continued)

more other anatomical structures in the thoracic cavity; abating one or more portions of the coronary structure in the 3D representation that attenuate visualization of the coronary arterial tree; generating, by maximum intensity projection (MIP), a plurality of MIP images of the coronary structure from the 3D representation; and compositing the MIP images to generate the panoramic visualization of the coronary arterial tree.

18 Claims, 7 Drawing Sheets

(51) Int. Cl.
| | |
|---|---|
| *G06T 5/40* | (2006.01) |
| *G06T 7/11* | (2017.01) |
| *G06T 11/40* | (2006.01) |
| *A61B 6/00* | (2006.01) |
| *A61B 6/03* | (2006.01) |

(52) U.S. Cl.
CPC .............. *A61B 6/5223* (2013.01); *G06T 5/40* (2013.01); *G06T 7/11* (2017.01); *G06T 11/40* (2013.01); *G06T 15/08* (2013.01); *G06T 2207/10081* (2013.01); *G06T 2207/20156* (2013.01); *G06T 2207/30048* (2013.01); *G06T 2207/30101* (2013.01); *G06T 2211/404* (2013.01); *G06T 2219/2012* (2013.01); *G06T 2219/2016* (2013.01)

(58) Field of Classification Search
CPC ........... G06T 2207/10081; G06T 19/20; G06T 15/08; G06T 2219/2012; G06T 2219/2016; G06T 7/11; G06T 5/40; G06T 2207/20156; G06T 2207/30048; A61B 6/466; A61B 6/5223; A61B 6/032; A61B 6/504
USPC .................................................. 382/130, 131
See application file for complete search history.

(56) References Cited

U.S. PATENT DOCUMENTS

2010/0296709 A1* 11/2010 Ostrovsky-Berman ...................... G06T 7/11
382/128
2012/0134564 A1* 5/2012 Zheng ..................... G06T 7/149
382/131

OTHER PUBLICATIONS

Wang, Chunliang, et al. "An interactive software module for visualizing coronary arteries in CT angiography." International Journal of Computer Assisted Radiology and Surgery 3.1-2 (2008): 11-18. (Year: 2008).*
Ooi, Thean Wui, Haidi Ibrahim, and Kenny Kal Vin Toh. "Implementation of several rendering and volume rotation methods for volume rendering of 3D medical dataset." 2008 IEEE Conference on Innovative Technologies in Intelligent Systems and Industrial Applications. IEEE, 2008. (Year: 2008).*
Lell, Michael M., et al. "New techniques in CT angiography." Radiographics 26.suppl_1 (2006): S45-S62. (Year: 2006).*
Wang, Chunliang, and Orjan Smedby. "Integrating automatic and interactive methods for coronary artery segmentation: let the PACS workstation think ahead." International journal of computer assisted radiology and surgery 5.3 (2010): 275-285. (Year: 2010).*
Hemmati, H. R., et al. "Segmentation of carotid arteries in computed tomography angiography images using fast marching and graph cut methods." 2013 21st Iranian Conference on Electrical Engineering (ICEE). IEEE, 2013. (Year: 2013).*
Achenbach, et al., "Contrast enhanced electron beam computed tomography to analyse the coronary arteries in patients after acute myocardial infarction," Heart, 2000, pp. 489-493, vol. 84.
Addis, et al., "CT Angiography: In Vitro Comparison of Five Reconstruction Methods," American Journal of Roentgenology, Nov. 2001, pp. 1171-1176, vol. 177, American Roentgen Ray Society.
Canny, et al., "A Computational Approach to Edge Detection," IEEE Transactions on Pattern Analysis and Machine Intelligence, Nov. 1986, pp. 679-698, vol. PAMI-8, No. 6, IEEE.
Chi, et al., "A Composite of Features for Learning-Based Coronary Artery Segmentation on Cardiac CT Angiography," LNCS 9352, 2015, pp. 271-279, Springer International Publishing Switzerland.
Cline, et al., "Combined Connectivity and a Gray-Level Morphological Filter in Magnetic Resonance Coronary Angiography," Magnetic Resonance in Medicine, 2000, pp. 892-895, vol. 43, Wiley-Liss, Inc.
Ferencik, et al., "Diagnostic Accuracy of Image Postprocessing Methods for the Detection of Coronary Artery Stenoses by Using Multidetector CT," Radiology, Jun. 2007, pp. 696-702, vol. 243, No. 3.
Fishman, et al., "Volume Rendering versus Maximum Intensity Projection in CT Angiography: What Works Best, When, and Why," RadioGraphics 2006, pp. 905-922, vol. 26, RSNA.
Jinzaki, et al., "Diagnostic Accuracy of Angiographic View Image for the Detection of Coronary Artery Stenoses by 64-Detector Row CT: A Pilot Study Comparison With Conventional Post-Processing Methods and Axial Images Alone," Circulation Journal, Apr. 2009, pp. 691-698, vol. 73.
Johnson, et al., "Renal Artery Stenosis: CT Angiography—Comparison of Real-time Volume-rendering and Maximum Intensity Projection Algorithms," Radiology, 1999. pp. 337-343, vol. 211.
Lin, et al., "Development of a Computer Algorithm-Based Method for Identification of Blood Vessels on Dynamic Contrast Enhanced Breast MRI," Proceedings of the International Society for Magnetic Resonance in Medicine, 2009, 1 page, vol. 17.
Napel, et al., "CT Angiography with Spiral CT and Maximum Intensity Projection," Radiology, 1992, pp. 607-610, vol. 185, RSNA.
Pizer, et al., "Adaptive Histogram Equalization and Its Variations," Computer Vision, Graphics, and Image Processing, 1987, pp. 355-368, vol. 39, Academic Press, Inc.
The Extended European Search Report for Application No. 17776010.5 dated Sep. 27, 2019, 11 pages.
The International Search Report for PCT Application No. PCT/SG2017/050185 dated Jun. 27, 2017, 3 pages.
The Written Opinion of the International Searching Authority for PCT Application No. PCT/SG2017/050185 dated Jun. 27, 2017, 4 pages.
Van Ooijen, et al., "Coronary Artery Imaging with Multidetector CT: Visualization Issues," RadioGraphics, 2003, 12 pgs., vol. 23, No. 6, Radiological Society of North America, <https://doi.org/10.1148/rg.e16>.
Vogl, et al., "Techniques for the Detection of Coronary Atherosclerosis: Multi-detector Row CT Coronary Angiography," Radiology, 2002, pp. 212-220, vol. 223, RSNA.
Wang, et al., "Can segmented 3D images be used for stenosis evaluation in coronary CT angiography?" Acta Radiologica, 2012, pp. 845-851, vol. 53, No. 8, <http://dx.doi.org/10.1258/ar.2012.120053>.

* cited by examiner

|  | LAD | LCX | RCA |
|---|---|---|---|
| (a) Invasive CCA |  |  |  |
| (b) Panoramic Visualization |  |  |  |
| (c) Magnified Panoramic Visualization |  |  |  |

PANORAMIC VISUALIZATION OF CORONARY ARTERIAL TREE

CROSS-REFERENCE TO RELATED APPLICATIONS

This patent application is a U.S. National Phase Application under 35 U.S.C. § 371 of International Application No. PCT/SG2017/050185, filed on 31 Mar. 2017, entitled PANORAMIC VISUALIZATION OF CORONARY ARTERIAL TREE, which claims the benefit of Singapore Patent Application No. 10201602554s, filed on 31 Mar. 2016, which was incorporated in its entirety by reference herein.

TECHNICAL FIELD

The present disclosure generally relates to panoramic visualization of coronary arterial tree. More particularly, the present disclosure describes various embodiments of an automated method and system for generating a panoramic visualization of a coronary arterial tree of a subject (e.g. human patient or candidate).

BACKGROUND

References

[1] M. Ferencik, D. Ropers, S. Abbara, R. C. Cury, U. Hoffmann, K. Nieman, T. J. Brady, F. Moselewski, W. G. Daniel, and S. Achenbach, "Diagnostic Accuracy of Image Postprocessing Methods for the Detection of Coronary Artery Stenoses by Using Multidetector CT 1," Radiology, vol. 243, no. 3, pp. 696-702, 2007.

[2] (C. Wang, A. Persson, J. Engvall, J. De Geer, W. Czekierda, A. Björkholm, S.-G. Fransson, and Ö. Smedby, "Can segmented 3D images be used for stenosis evaluation in coronary CT angiography?," Acta Radiol., vol. 53, no. 8, pp. 845-851, 2012.

[3] E. K. Fishman, D. R. Ney, D. G. Heath, F. M. Corl, K. M. Horton, and P. T. Johnson, "Volume rendering versus maximum intensity projection in CT angiography: what works best, when, and Why1," Radiographics, 2006.

[4] P. T. Johnson, E. J. Halpern, B. S. Kuszyk, D. G. Heath, R. J. Wechsler, L. N. Nazarian, G. A. Gardiner, D. C. Levin, and E. K. Fishman, "Renal Artery Stenosis: CT Angiography—Comparison of Real-time Volume-rendering and Maximum Intensity Projection Algorithms 1," Radiology, vol. 211, no. 2, pp. 337-343, 1999.

[5] S. Napel, M. P. Marks, G. D. Rubin, M. D. Dake, C. H. McDonnell, S. M. Song, D. R. Enzmann, and R. B. Jeffrey Jr, "CT angiography with spiral CT and maximum intensity projection," Radiology, vol. 185, no. 2, pp. 607-610, 1992.

[6] T. J. Vogl, N. D. Abolmaali, T. Diebold, K. Engelmann, M. Ay, S. Dogan, G. Wimmer-Greinecker, A. Moritz, and C. Herzog, "Techniques for the Detection of Coronary Atherosclerosis: Multi-detector Row CT Coronary Angiography 1," Radiology, vol. 223, no. 1, pp. 212-220, 2002.

[7] K. A. Addis, K. D. Hopper, T. A. Iyriboz, Y. Liu, S. W. Wise, C. J. Kasales, J. S. Blebea, and D. T. Mauger, "CT angiography: in vitro comparison of five reconstruction methods," Am. J. Roentgenol., vol. 177, no. 5, pp. 1171-1176, 2001.

[8] S. M. Pizer, E. P. Amburn, J. D. Austin, R. Cromartie, A. Geselowitz, T. Greer, B. ter Haar Romeny, J. B. Zimmerman, and K. Zuiderveld, "Adaptive histogram equalization and its variations," Comput. Vis. Graph. Image Process., vol. 39, no. 3, pp. 355-368, 1987.

[9]. Canny, "A computational approach to edge detection," Pattern Anal. Mach. Intell. IEEE Trans. On, no. 6, pp. 679-698, 1986.

Many people worldwide suffer from coronary artery disease (CAD) or coronary heart disease (CHD). Also known as ischemic heart disease (IHD), CHD is a group of diseases that includes stable angina, unstable angina, myocardial infarction, and sudden cardiac death. CHD is the leading cause of death globally and a major contribution to health care costs. Cardiac or coronary computed tomography angiography (CTA) is a common diagnosis imaging modality and acquired in the form of cross-sectional images or slices. These slices are then stacked to form a three-dimensional (3D) volume. The 3D volume thus includes a stack of thin two-dimensional (2D) volume dataset having a stack of thin 2D axial/transverse images of finite thickness. A radiographer technologist post-processes the 2D images, cropping manually to produce the 3D volume that is then software volume-rendered (VR). While VR is visually very attractive because it gives a realistic shaded colour display of vessels and their structural relations in 3D, VR is dependent on software algorithms which may not be uniform among vendors. Moreover, quantitation of coronary stenosis is not done on VR but on the images as it is perceived to be least predisposed to post-processing artifacts; the 3D volume itself is never used for quantitative coronary artery stenosis analysis and for assessing CHD.

To assess whether an individual has CHD, it is desirable to visualize intuitively and quantify accurately the coronary arteries. A wide variety of medical image processing techniques have been developed to visualize and quantify the coronary arteries around the heart. However, these techniques are based on the segmentation or centre line extraction of the coronary arteries, which is difficult because of the vessel's pathology, size, position, anatomical structure, and variances.

In recent years, the amount of CTA data to be evaluated has grown considerably. Computerized tomography (CT) and CTA datasets used to be assessed via transverse images. Recently, advanced image post-processing methods, such as maximum intensity projection (MIP), curved planar reformation (CPR), the multiplanar projection reformation (MPR), and volume rendering technique (VRT), have been often used to assist evaluation of CT and CTA datasets in clinical practice. MPR of coronary segments of interest requires some skill to manipulate to get the optimum angle for depicting the lesion and is time-consuming for multiple vessels. CPR may be performed to quantify stenosis, but it is even more time-consuming and is operator-dependent as the output is affected by the manual delineation of the vessel path. Conventionally, MIP has been used for non-coronary vessel quantitative analysis or vascular visualization from 3D datasets; MIP is not used in CTA because of interfering noise signals from the left ventricular cavitary blood. Diagnostic accuracies from using these post-processing methods have also been studied.

Ferencik et al. conducted the stenosis detection using free oblique MPRs, free oblique MIPs, and pre-rendered VTR on CTA datasets of 40 patients, and obtained accuracies for detecting stenosis of 91%, 86%, and 73%, respectively. Wang et al. compared two coronary artery segmentation algorithms in terms of stenosis evaluation on CTA datasets of 30 patients and obtained an accuracy of 71% for their proposed method and 74% for the radiologist's evaluation. Fishman et al. compared the performance of VRT and slab-editing MIP when used in various clinical practices, and concluded that both techniques need to be used together in evaluating images in order obtain a comprehensive understanding. Johnson et al. compared VRT and MIP on renal artery stenosis evaluation of CTA datasets of 25 patients and obtained a sensitivity of 89% and 94%, and a specificity of 99% and 87%, respectively. Napel et al. illustrated that MIP had excellent anatomic correlation with conventional angiography. Vogl et al. studied 64 patients and reported axial scans showed the sensitivity of 73.4% in the evaluation of stenosis, and MPRs of 46.8%. Addis et al. studied 19 vessel phantoms and showed that measurements based on transverse images, MIP, MPR, VRT techniques had errors of less than 2.5% for those vessels greater than 4 mm in diameter. In estimating vessels smaller than 4 mm in diameter, transverse images, MIP, MPR, and shaded-surface display techniques resulted in a measurement error of more than 10%, while VRT resulted in a measurement error of 2.5% to 10%.

These post-processing methods have been used to assist the evaluation of CT images. Although they are prone to lose information compared with the original images, researchers agree that experienced radiologists are able to achieve good reproducibility when supported by advanced vessel analysis software. Further research showed that post-processing methods are useful to assist the radiologist in identifying the location of the greatest narrowing. Nonetheless, researchers have different suggestions regarding the usage of post-processing methods. Some suggested that the diagnostic evaluation was conducted on MPR, CPR, or MIP images with the assistance of VRT. Others suggested that the diagnostic evaluation be conducted on CT images with the assistance of the advanced image display methods. Generally, the research indicates that post-processing methods are helpful in quantitative coronary analysis, but arguments remain about the efficiencies of these methods.

These studies thus demonstrate the potential of post-processing methods for facilitating diagnosis and improving diagnostic accuracy. However, a common consensus is lacking on which individual post-processing method is most effective on improving diagnostic accuracy. Moreover, as evaluated in these studies, MIP was in the form of non-editing or slab-editing MIP which generates lateral views and displays two-dimensional (2D) localized information only. The 2D localized information from MIP does not show how information from different images is related to one another, thereby failing to provide overall information of the coronary region.

Therefore, in order to address or alleviate at least one of the aforementioned problems and/or disadvantages, there is a need to provide an automated method and system for generating a panoramic visualization of a coronary arterial tree of a subject, in which there is at least one improvement and/or advantage over the aforementioned prior art.

SUMMARY

According to an aspect of the present disclosure, there is an automated method and system for generating a panoramic visualization of a coronary arterial tree of a subject. The system comprises a processor configured for performing steps of the method. Steps of the method comprise: acquiring an image volume of a thoracic cavity of the subject, the image volume providing a three-dimensional (3D) representation of the thoracic cavity; isolating a coronary structure in the 3D representation by abating one or more other anatomical structures in the thoracic cavity; abating one or more portions of the coronary structure in the 3D representation that attenuate visualization of the coronary arterial tree; generating, by maximum intensity projection (MIP), a plurality of MIP images of the coronary structure from the 3D representation; and compositing the MIP images to generate the panoramic visualization of the coronary arterial tree.

An advantage of the present disclosure is that the panoramic visualization is able to convey 3D structure of the coronary arterial tree. The panoramic visualization allows the 3D relationships between vessels in the coronary arterial tree to be appreciated more readily. The panoramic visualization is thus capable of complete coronary artery visualization and quantification without coronary artery segmentation. One potential application of the panoramic visualization is to detect and quantify the stenosis of coronary arteries, comparable to conventional coronary angiography (CCA) images.

An automated method and system for generating a panoramic visualization of a coronary arterial tree of a subject according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "I" in a figure or associated text is understood to mean "and/or" unless otherwise indicated. The recitation of a particular numerical value or value range herein is understood to include or be a recitation of an approximate numerical value or value range.

For purposes of brevity and clarity, descriptions of embodiments of the present disclosure are directed to an automated method and system for generating a panoramic visualization of a coronary arterial tree of a subject, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

Figure 1:
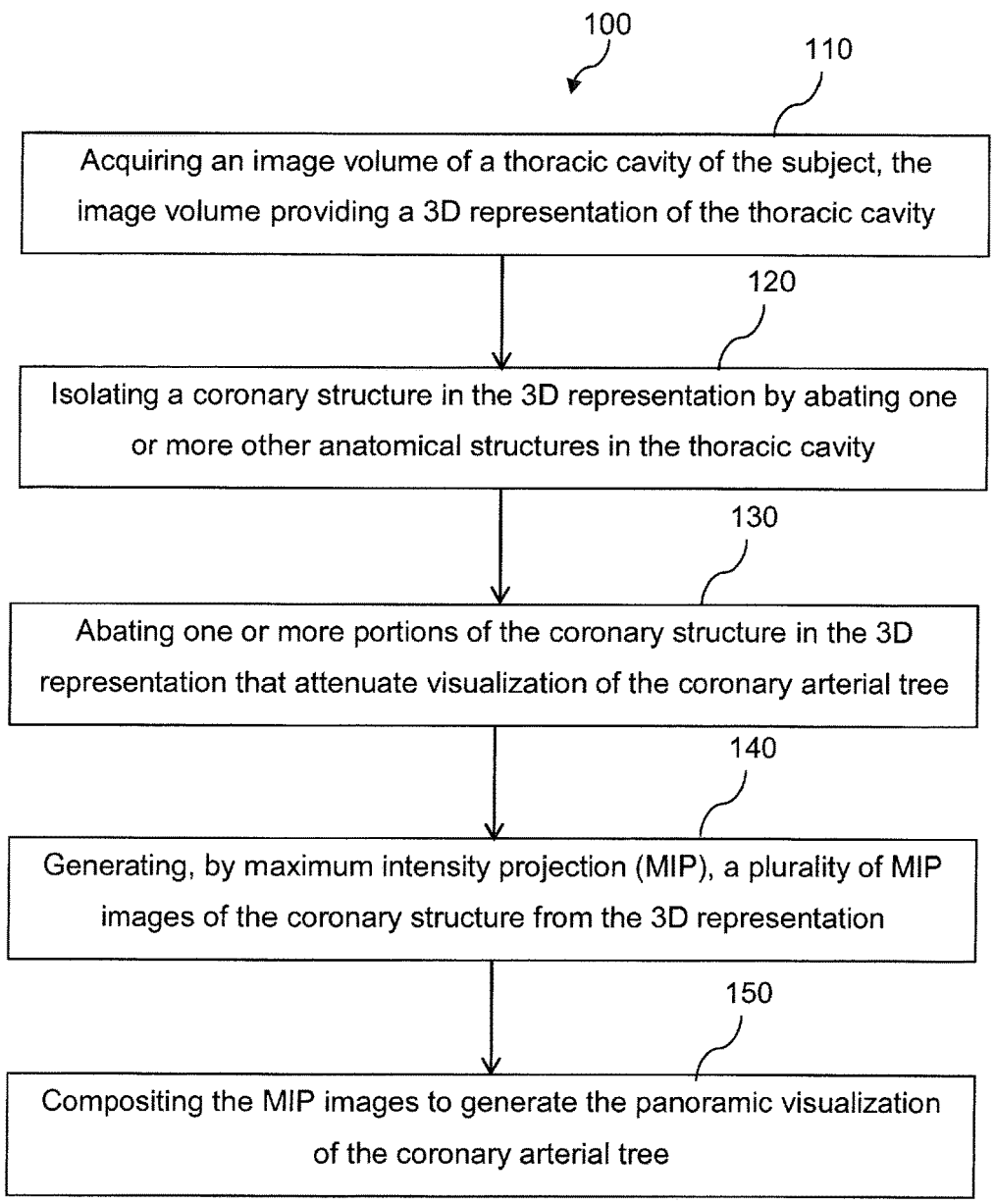
FIG. 1 illustrates a flowchart of a method for generating a panoramic visualization of a coronary arterial tree of a subject.

In representative or exemplary embodiments of the present disclosure, there is a system including a processor for performing an automated method 100 for generating a panoramic visualization of a coronary arterial tree of a subject. With reference to FIG. 1, the method 100 includes a step 110 of acquiring an image volume of a thoracic cavity of the subject, the image volume providing a 3D representation of the thoracic cavity. The image volume may be captured by an imaging modality such as CTA. Multiple 2D images or slices are stacked together to collectively form the image volume. Each 2D image has a finite thickness and represents an axial/transverse image of the thoracic cavity. The image volume is thus a 3D volume that provides the 3D representation of the thoracic cavity.

The thoracic cavity (or chest cavity) is a chamber in the body of the subject that contains a number of anatomical structures. For example, the thoracic cavity contains structures of the cardiovascular system including at least the heart, great vessels, and coronary arterial tree. The thoracic cavity also contains structures of the respiratory system including at least the lungs. The thoracic cavity also contains bone structures such as the rib cage. In some cases, as the liver is positioned close to the heart, the 3D representation of the thoracic cavity may include representations of some liver tissue.

The method 100 includes a step 120 of isolating a coronary structure in the 3D representation by abating one or more other anatomical structures in the thoracic cavity. The coronary structure collectively refers to the structures of the cardiovascular system, i.e. including the heart, great vessels, and coronary arterial tree. The one or more other anatomical structures in the thoracic cavity may include the lungs, bone structures, and/or liver tissue.

The method 100 includes a step 130 of abating one or more portions of the coronary structure in the 3D representation that attenuate visualization of the coronary arterial tree. These one or more portions of the coronary structure may introduce noise signals that attenuate, e.g. compromise or reduce the quality of, the visualization of the coronary arterial tree. They may include one or more chambers of the heart.

The method 100 includes a step 140 of generating, by maximum intensity projection (MIP), a plurality of MIP images of the coronary structure from the 3D representation. Generally, MIP is a volume rendering method for 3D data that projects, onto a visualization plane, the voxels with maximum intensity, i.e. brightest, that fall in the way of parallel rays traced from the viewpoint to the projection plane.

Figure 2:
FIG. 2 illustrates a panoramic visualization of the coronary arterial tree generated by automated segmentation of the heart region.

The method 100 includes a step 150 of compositing the MIP images to generate the panoramic visualization of the coronary arterial tree. The MIP images represent various views of the coronary structure, and preferably collectively represent a wide-angle or 360° overall view that covers all segments of the coronary structure. The MIP images are composited, i.e. combined or stitched, together to form the panoramic visualization that is able to convey the 3D structure of the coronary arterial tree. An example illustration of the panoramic visualization of the coronary arterial tree is shown in FIG. 2.

Figure 3:
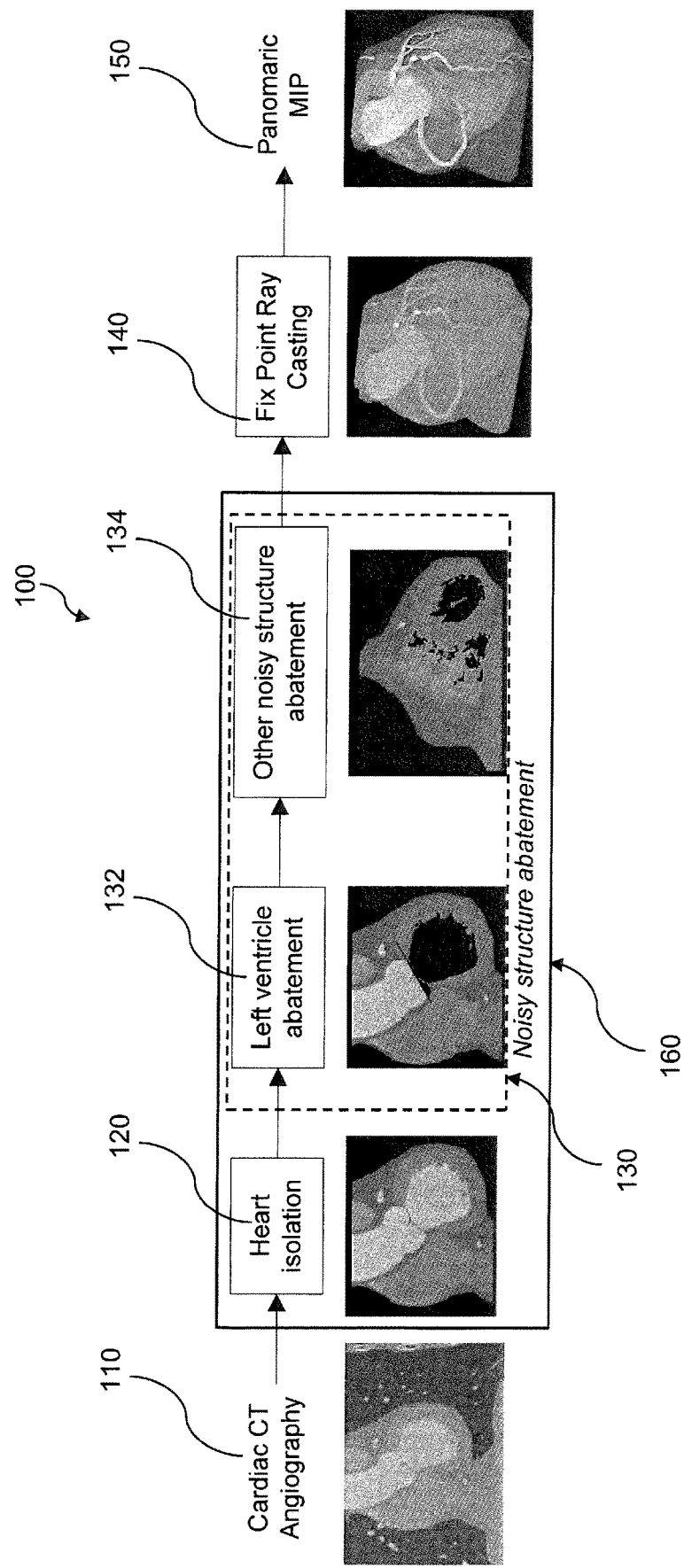
FIG. 3 illustrates another flowchart of the method for generating a panoramic visualization of a coronary arterial tree of a subject.

In some embodiments, an implementation of the method 100 is described with reference to FIG. 3. The method 100 includes the step 110 of acquiring a CTA image volume of the thoracic cavity of the subject, the CTA image volume providing a 3D representation of the thoracic cavity.

The method 100 includes the step 120 of isolating a coronary structure in the 3D representation by abating one or more other anatomical structures in the thoracic cavity. The coronary structure refers to the heart region of the subject that includes the heart, great vessels, and coronary arterial tree. The heart region is isolated and extracted by abating other anatomical structures such as the lungs and bones, and more specifically by using a compact method, as described in more detail below.

Figure 4:
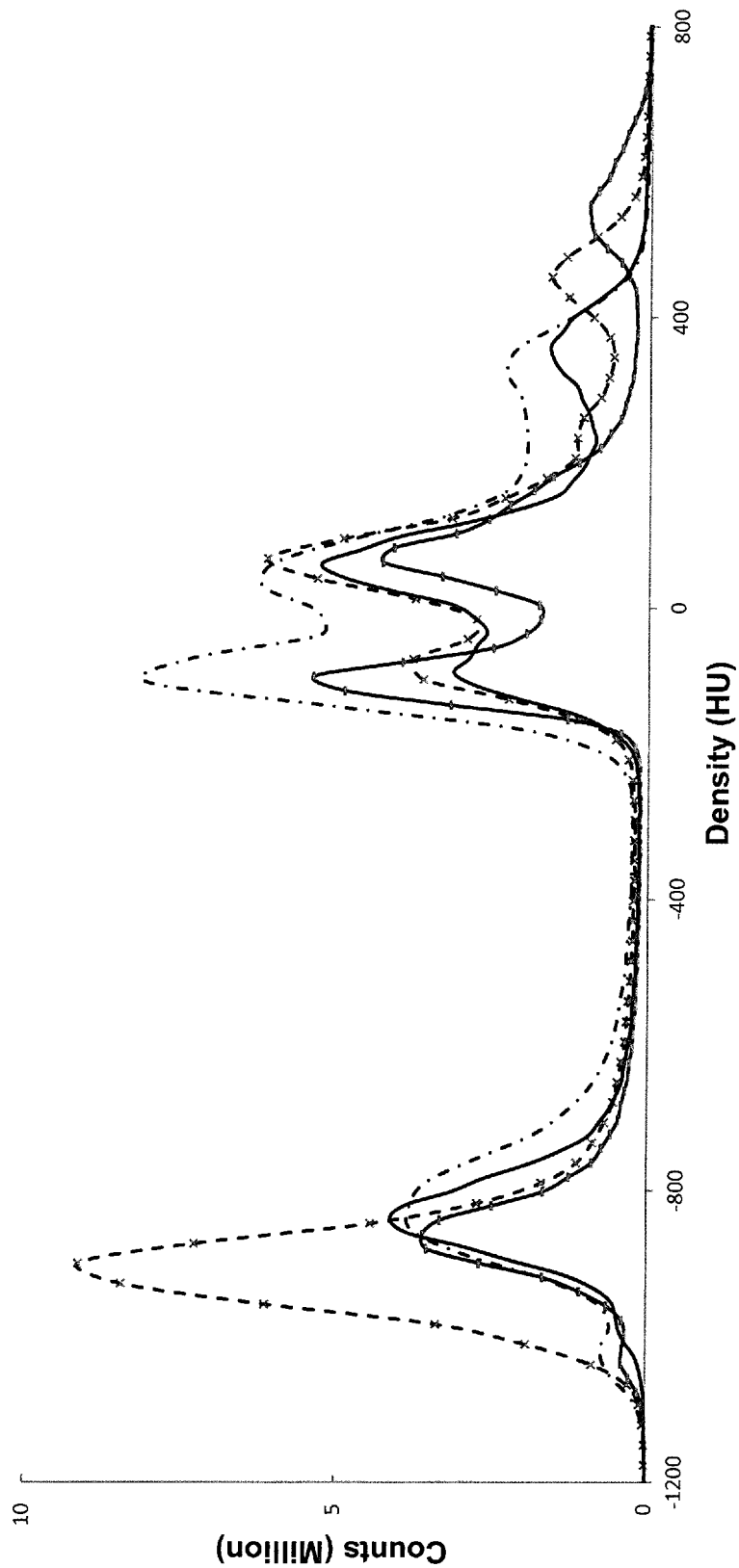
FIG. 4 illustrates a density histogram of CTA images.

The step 120 includes a thresholding operation, an erosion operation, and a dilation operation to isolate and extract the heart region in the 3D representation. FIG. 4 illustrates a density histogram of four CTA image volumes. In the thresholding operation with reference to a density histogram of four CTA image volumes as shown in FIG. 4, the threshold is set to a value of −400 HU (Hounsfield unit), which is between the density of air (−1000 HU) and fat (−100 HU). Notably, the density of lung is −500 HU and the density of bone is 700 HU. Voxels in 3D representation with density higher than the threshold value are set as foreground data and the remaining voxels (abated data from the lungs and bones based on the threshold value) are set as background data or noise. The thresholding value thus differentiates foreground information and background information to provide an initial heart mask.

In the erosion operation, some vessel-like structural elements in the heart region are abated or eliminated by introducing a structural element in the shape of a disc with a predetermined radius value, e.g. 6 mm. As the abatement or elimination of these vessel-like structural elements may affect the size of the initial heart mask, the dilation operation may be performed with the same structural element to restore the heart mask to its initial size.

Starting from a bounding box manually selected on one slice, the heart region is cropped slice by slice in the axial/transverse view using the meanshift/camshift based technique. A bounding box is manually selected on an initial slice where the heart is widest from left to right. The contour from heart region foreground within the bounding box is used to detect the heart region in the next slice. The meanshift/camshift based technique finds the best match of the heart region contour on the next slice to detect and propagate the cropping to the other slices. In each slice, the contour of the cropped heart region is used as the "bounding box" for the next slice. The meanshift/camshift based technique assumes small changes of the of the heart region contour slice by slice. The processing stops at the predetermined top and bottom slices and the entire heart region can be isolated and extracted. In the processed CTA image volume, the heart region remains at its original density, while the background is abated to −1000 HU. An example of the pseudocode for this processing is shown in the box below.

arterial tree. However, in another embodiment, various operations may be taken to abate or exclude the liver tissue from the heart region.

Figure 5:
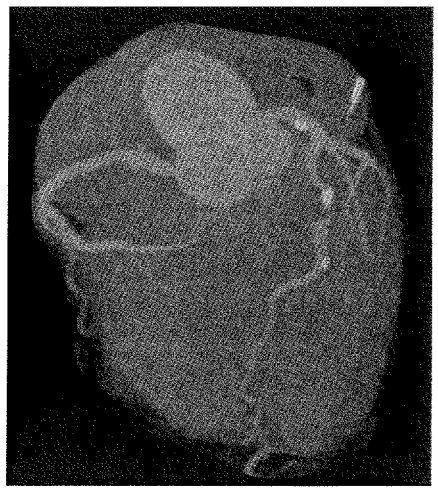
FIG. 5 illustrates a panoramic visualization of the coronary arterial tree by manual segmentation of the heart region.

FIG. 2 illustrates a panoramic visualization of the coronary arterial tree generated by the automated method 100 wherein the heart region is isolated and segmented using the meanshift/camshift based technique. FIG. 5 illustrates a panoramic visualization of the coronary arterial tree by manually delineating and segmenting the heart region. Comparing between the visualizations in FIG. 2 and FIG. 5, it can

```
Start
    Initializing... HBB = Heart bounding box, Initial Slice
    T_lung = − 400 Hu;
    D_background = −1000 Hu;
    If CTAImage>T_lung and CTAImage in HBB
            Foreground = 1;
    Else
        Foreground = 0;
    End
    Se = StructuralElement ('disk', 6mm);
    Foreground = Erosion(Foreground,Se);
    Foreground = Dilation(Foreground, Se);
    InitialHeartMask = BiggestConnectedComponentofForeground (InitialSlice);
    [Wx, Wy] = LeftTop(InitialHeartMask);
    [Lx, Ly] = Length(InitialHeartMask);
    SX = Wx-1; EX = SX + Lx; SY = Wy-1; EY = SY + Ly;
    Ratio = Ly/Lx;
    HeartMask(SX: EX, SY: EY, InitialSlice) = Foreground(SX: EX, SY: EY,
    InitialSlice);
    For num = InitSlice+1 : EndSlice
        TemplatefromPreviousSlice = HeartMask(SX: EX, SY: EY, num−1);
        CK = centroid(TemplatefromPreviousSlice);
          While Flag_MeanConverging
                Object = Foreground(SX:EX, SY: EY, num);
                Intersection = and(Object, TemplatefromPrevious);
                C = Centroid(Intersection);
                offset = C−CK;
                [SX SY] = [SX SY] + offset; [EX EY] = [EX EY] +offset;
                If (offset<T_offset or n_Iterations<1)
                    Flag_MeanConverging = 0;
                End
            End
            Object = BiggestConnectedComponent(Foreground(SX: EX, SY: EY,
num));
            HeartMask(SX: EX, SY: EY,num) = and(Object,
TemplatefromPreviousSlice);
            [Wx, Wy] = LeftTop(Object);
            [Lx, Ly] = Length(Object);
            SX = Wx-1; EX = SX + Lx; SY = Wy-1; EY = SY + Ly;
            Loffset = Ly − Lx*ratio;
            EY = EY − Loffset;
    End
    For num = InitSlice−1 : −1 : StartSlice
            Repeat operations in the above for loop.
    End
    Se = StructureElement('disk',3);
    Dilation (HeartMask, Se);
    If (HeartMask>0)
            Heart = CTAImage;
    Else
        Heart = D_background;
            End
            Saving... Heart, HeartMask
End
```

The isolation of the heart region works well to abate the lungs and bones, e.g. rib cage. However, the heart region may also include some liver tissue as the liver is positioned close to the heart. In one embodiment, the step 120 abates the lungs and bones but does not process the heart region further to abate or exclude the liver tissue. The liver is a low attenuating structure with a density of 40 to 60 HU, which is lower than that of the heart region. It is unlikely that the presence of liver tissue in small amounts in the heart region would affect the resultant visualization of the coronary be observed that the manually segmented heart region can result in similar visualization of the coronary arterial tree as that from the automated method 100. There is thus a low requirement for accurate isolation of the heart region in the step 120 and this is advantageous because the automated method 100 can achieve the desired visualization results with low computational complexity and minimal reduction in effectiveness.

The method 100 includes the step 130 of abating one or more portions of the coronary structure in the 3D representation that attenuate visualization of the coronary arterial tree. The step 130 includes segmenting each portion from the coronary arterial tree with a separation disc, and subsequently flood filling each portion with a seed point. The one or more portions of the coronary structure includes the left ventricle chamber of the heart region. The left ventricle is a high attenuating structure that introduces unwanted noise or bright signals to the visualization of the coronary arterial tree.

Figure 6:
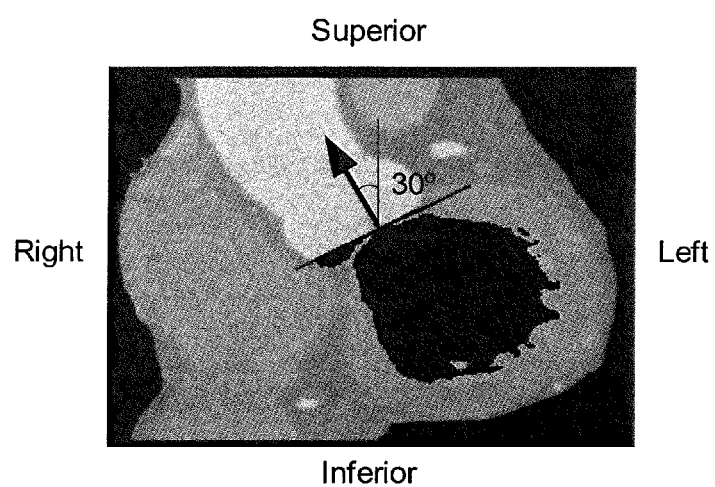
FIG. 6 illustrates abatement of the left ventricle from the heart region.

The step 130 includes a step 132 of abating the left ventricle. Based on the 3D representation from the CTA image volume, the left ventricle is segmented from the coronary arterial tree, specifically the aorta, with the separation disc. A software method such as ITK-SNAP may be used to perform this image segmentation. The ascending aortic diameter has an upper limit of approximately 42.6 mm, and the aortic insertion angle on the left ventricle ranges from approximately 30° to 60°. Thus, the separation disc with a 50 mm diameter placed on the aortic valve is able to separate the left ventricle from the aorta. The normal direction of the separation disc is approximately 30° to the right of the inferior-superior axis as shown in FIG. 6.

To abate the left ventricle segmented from the aorta, the left ventricle is flood filled with a seed point and a threshold value. A Gaussian mixture model (GMM) may be employed to determine the threshold value for the flood fill. The GMM first models the intensity distribution of the CTA images in the image volume. The threshold value is set as $(\mu_1-\Sigma_1)$, where $\mu_1$ and $\Sigma_1$ refer to the mean and covariance, respectively, of the first component of the GMM. In the step 130, the components of the GMM are ranked in mean density from high to low. With the threshold value determined, the left ventricle is flood filled with a seed point selected to initiate a region, i.e. the left ventricle, to start growing and abating. Consequently, the flood filling suppresses the left ventricle and abates it from the heart region. The left ventricle can thus be automatic cropped and abated to generate the desired volume of interest (heart region absent the left ventricle). This yields time savings and eliminates operator dependence.

Figure 7:
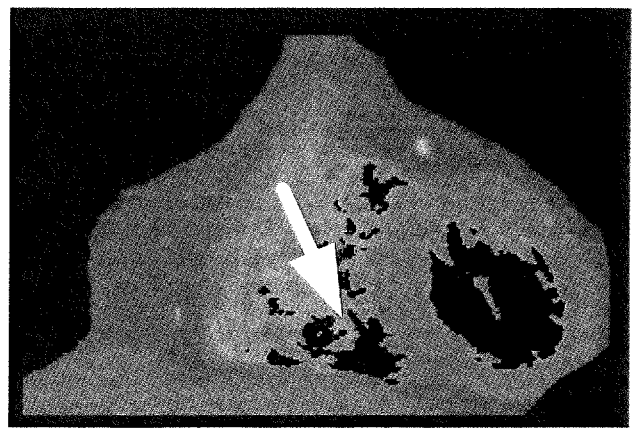
FIG. 7 illustrates abatement of other high attenuating structures from the heart region.

The method 100 further includes a step 134 of abating the other portions of the coronary structure or heart region. It will be appreciated that similar operations as those for the left ventricle, i.e. with the image segmentation and flood filling with the seed point, may be performed to suppress and abate said other portions of the heart region, particularly the high attenuating portions/structures thereof, as illustrated in an example in FIG. 7.

The steps 120 and 130 (including the steps 132 and 134) thus isolates the coronary structure or heart region by abating the other high attenuating structures in the heart region, such as the lungs, bones, and left ventricle. These high attenuating structures introduce unwanted noise or bright signals to the visualization of the coronary arterial tree. As shown in FIG. 3, these steps may be collectively referred to as a noisy structure abatement process 160.

The method 100 includes the step 140 of generating a plurality of MIP images of the coronary structure from the 3D representation. Notably, the coronary structure has at least the lungs, bones, and left ventricle abated from the heart region. As described above, MIP is a specific type of rendering in which the brightest voxel is projected into the MIP images. MIP is able to convey the densitometric information of the original CTA images without any parameters needing to be tuned and its implementation is relatively simple.

A fix point ray casting technique is employed to generate the MIP images. In this technique, a ray is generated for each projection plane. For simplicity, a camera model is used as an example to describe this fix point ray casting technique. The ray starts at the center of projection of the camera (also known as the viewpoint) and passes through the volume to be rendered, i.e. the 3D representation of the coronary structure. The ray is perpendicular to the projection plane. Along its parallel rays, MIP picks out the voxels with maximum intensity (brightest) and projects them on the visualization plane. The MIP images may also be referred to as the visualization images.

While the fix point ray casting technique can generate MIP/visualization images from a plurality of viewpoints, in this implementation of the fix point ray casting technique, the viewpoint is fixed and the projection plane is assumed to be the computer screen. As the viewpoint is fixed, the 3D representation of the coronary structure is rotatable on the computer screen in order to capture multiple views of the 3D representation in the MIP/visualization images. The 3D representation continues rotating and rendering the MIP/visualization images on the computer screen. The fix point ray casting technique is computationally fast such that it is able to render the MIP/visualization images in 2D during rotation of the 3D representation in real time. Optionally, the MIP images are enhanced by histogram equalization and rendered for improved visualization.

The method 100 includes the step 150 of compositing the MIP images to generate the panoramic visualization of the coronary arterial tree. The MIP images capture and represent multiple views of the 3D representation of the coronary structure, preferably over a complete 360° rotation. The composited MIP images are displayed in a cine loop resulting from continuous changes of the viewpoint to convey the 3D representation of the coronary structure and to provide the panoramic visualization of the coronary arterial tree. A user can thus visualize the coronary arterial tree panoramically without conducting vessel segmentation, thereby avoiding coping with serious stenosis and collateral vessels which can be quite challenging in vessel segmentation. In addition, the panoramic visualization enables localization of the greatest narrowing and measurement of the diameter stenosis by selecting an appropriate viewpoint.

An advantage of this panoramic visualization of the coronary arterial tree is that it is suitable for rapid demonstration of collateral vessels which is important in clinical diagnosis of CHD. In addition, with appropriate processing, the resulting high-contrast MIP images are directly comparable to CCA. Therefore, quantitative analysis of the coronary anatomy can be improved using the MIP images for panoramic visualization of the coronary arterial tree.

Coronary artery stenosis detection and quantification can be conducted based on the panoramic visualization of the coronary arterial tree. The performance and diagnostic accuracy of the panoramic visualization generated by the automated method 100 has been assessed for the detection and quantification of coronary artery stenosis in comparison with CCA with quantitative analysis as the reference standard.

Figure 8:
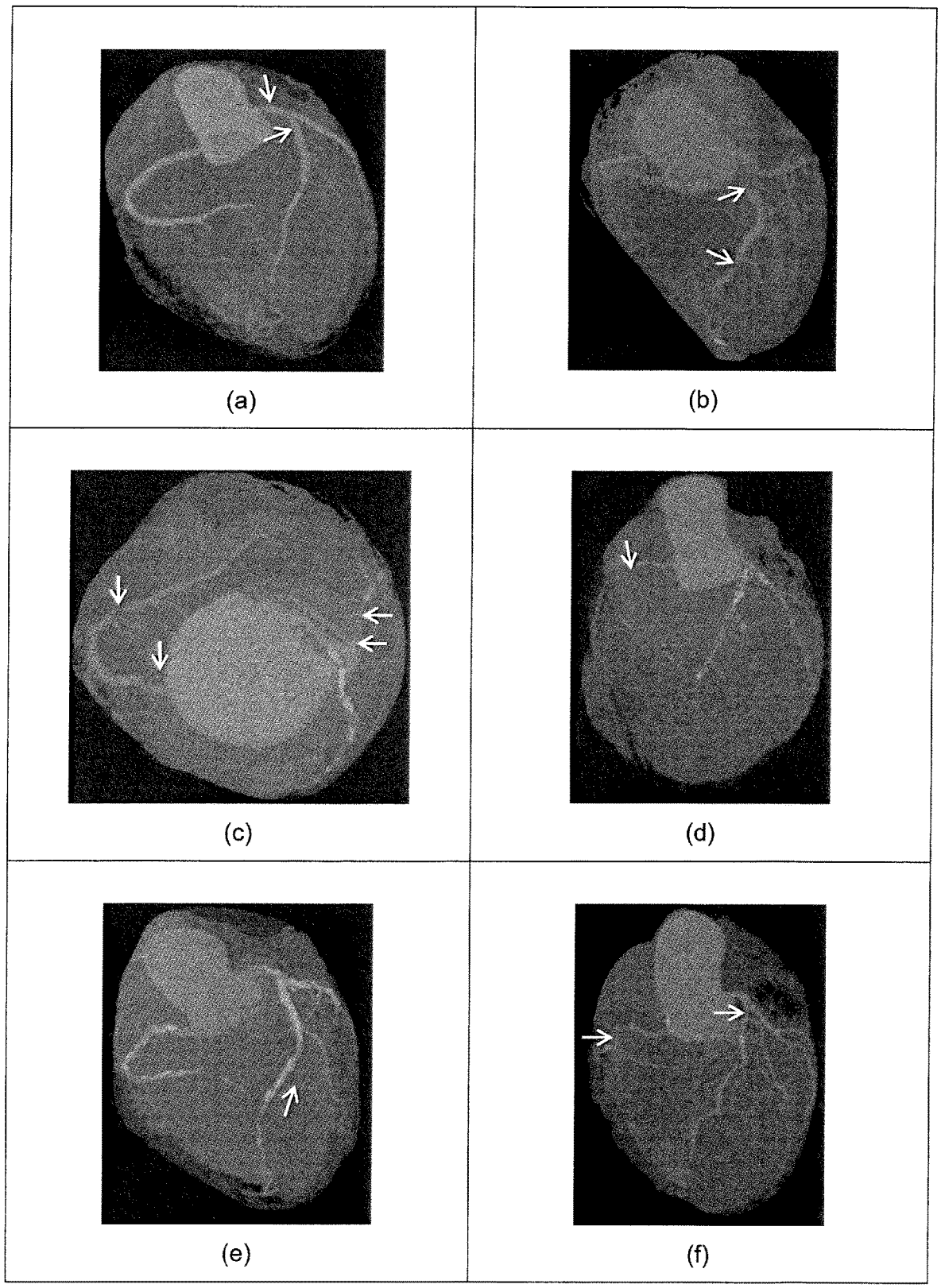
FIG. 8 illustrates panoramic visualizations of coronary arterial trees from various CTA image datasets.

Six anonymized CTA datasets from subjects with CHD are used for evaluation of the performance and diagnostic accuracy of the panoramic visualization generated by the automated method 100. The datasets are transferred to an offline workstation where they are prepared by an engineer with experience in CTA imaging for further evaluation. For each CTA dataset, the panoramic visualization is generated using the method 100 and rendered on the computer screen as shown in FIG. 8. The arrows indicate presence of stenosis.

The rendered panoramic visualization can be interactively viewed from any viewpoint or viewing angle by a mouse drag. The viewpoints are manually selected so that key coronary arterial tree information is visible. Through the panoramic visualization, the overall situation of the coronary arterial tree, including stenosis, calcification, branching, etc., can be observed intuitively.

Figure 9:
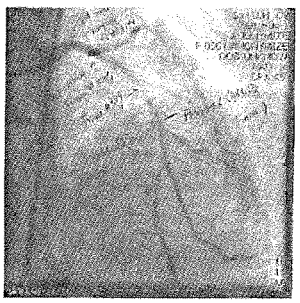
FIG. 9 illustrates a comparison of panoramic visualization images and CCA images.
Figure 9:
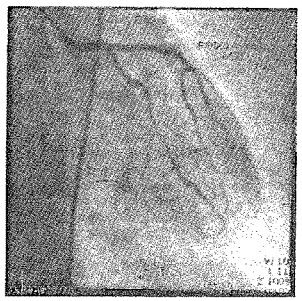
Figure 9:
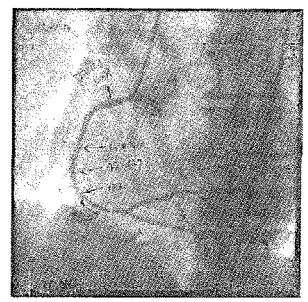
Figure 9:
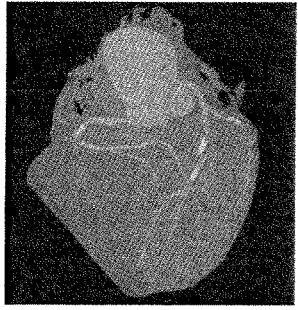
Figure 9:
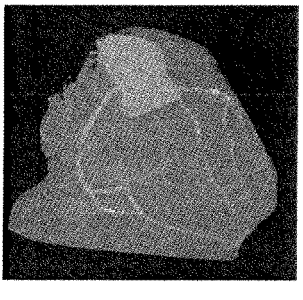
Figure 9:
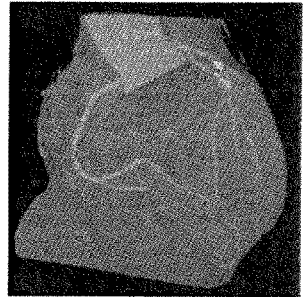
Figure 9:
Figure 9:
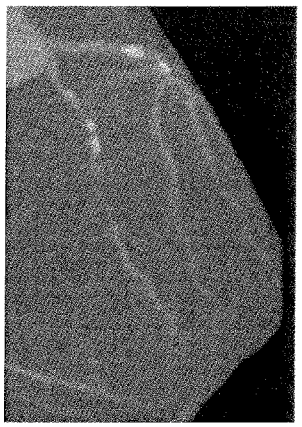
Figure 9:
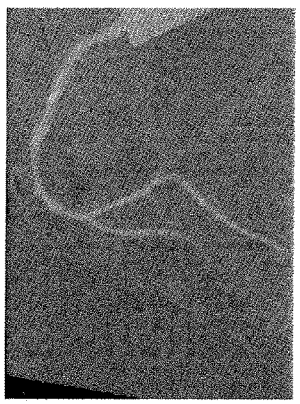

Corresponding to the each CTA dataset, the invasive CCA images and the clinical diameter stenosis (DS) measurements on CCA are also obtained as references. The comparison of the images is illustrated in FIG. 9. The top row shows the images obtained from invasive CCA, the middle row shows the images obtained from the panoramic visualization generated by the method 100, and the bottom row shows magnified versions of the images in the middle row. The images in the left column show the anterior interventricular artery or left anterior descending (LAD), the images in the middle column show the left circumflex artery (LCX), and the images in the right column show the right coronary artery (RCA).

The clinical measurements on the CCA images are used as the reference standard for stenosis detection. Lesions with a diameter reduction of 50% or more are considered as hemodynamically significant stenosis. In the comparison with CTA findings, 17 segments of coronary arterial tree are considered and the presence of stenosis is reported for each segment. The segment without lesions is reported as negative. The segment with lesions is reported as positive and is quantified in the CCA image.

Figure 10:
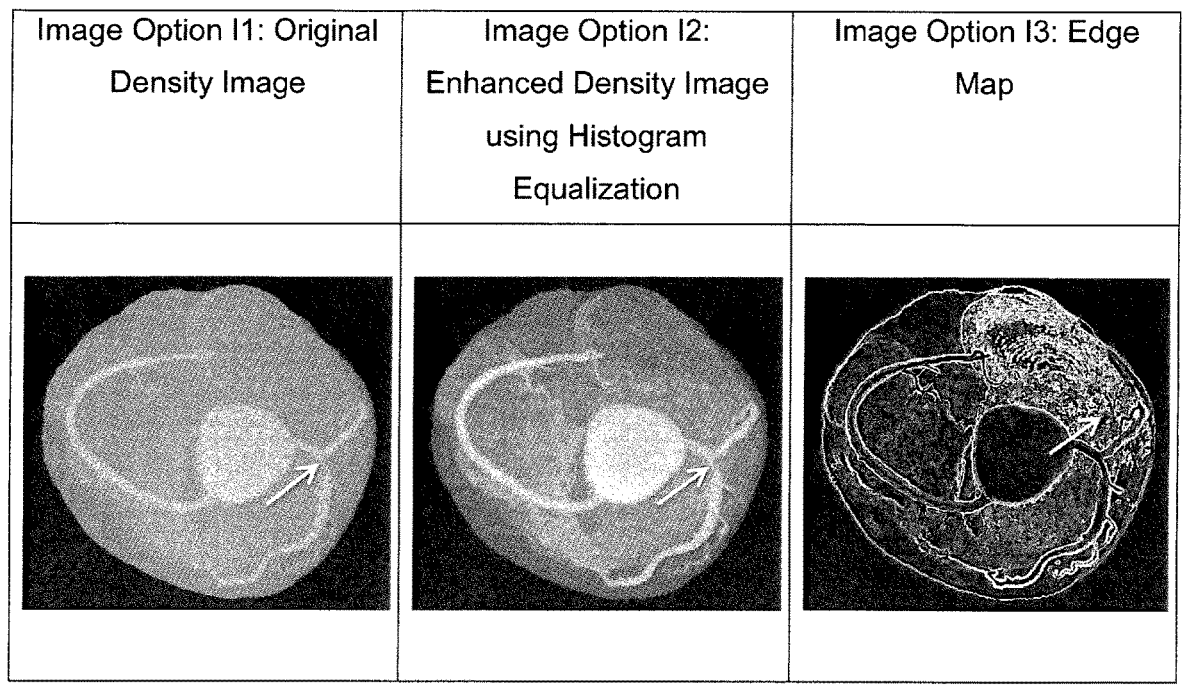
FIG. 10 illustrates three image options for viewing the panoramic visualization for stenosis quantification.

Some observers with experience in CTA imaging, who are not involved in the dataset preparation and are blinded to the CCA data, independently evaluated the six datasets on the same workstation by exclusively using the panoramic visualization generated by the method 100. The viewpoint of the panoramic visualization could be adjusted by the observers. Based on panoramic visualization from one viewpoint, three image options may be generated and provided for stenosis quantification—I1: original density image, I2: the density image enhanced using histogram equalization (see Pizer, et al.), and I3: the edge map extracted using the Canny edge detector (see Canny). Examples of images derived from the three image options are illustrated in FIG. 10. Their readings are based on the three image options respectively and include the coronary segment where the stenosis located, narrowest diameter, normal diameter, and each observer's favourite image option. For the measurement of the diameter, the system can automatically compute the distance of a line segment, and it requires the observers to draw a line segment representing the diameter. Measurements from the observers are recorded independently and separately. Two weeks later, the same observers evaluated the data again and the measurements are recorded.

The six datasets are evaluated for the presence of obstructive coronary stenosis at thresholds of 40%, 50%, 60%, and 70% stenosis. Each coronary arterial tree is assumed to consist of 17 segments. The evaluation results on each arterial segment are compared with those based on CCA. Performance of stenosis identification was evaluated by using sensitivity, specificity, and receiver operating characteristic (ROC) curve.

Figure 11:
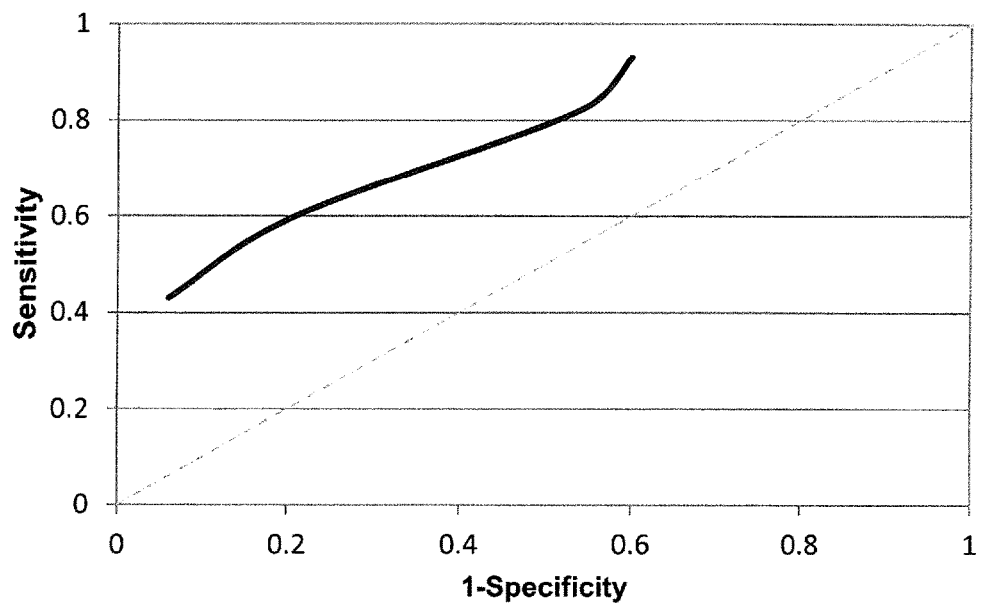
FIG. 11 illustrates a receiver operating characteristic curve of stenosis detection using panoramic visualization of the coronary arterial tree.

Sensitivity and specificity, compared with CCA, are calculated to evaluate the quantitative coronary analysis. In the results measured on the panoramic visualization, if only stenosis with a diameter reduction of 50% or more is considered, a sensitivity of 82% and a specificity of 95% are obtained. When the lower limit of diameter reduction was set as 40%, 50%, 60%, and 70%, a ROC curve of stenosis detection can be plotted as shown in FIG. 11. It can be found that the false positive rate reduced to 1% when serious stenosis (>70%) is considered. When the lower limit is reduced to 40%, a sensitivity of 93% can be reached. It is not practical to set an even lower limit (<40%) just to include more lesions because these lesions may be either hemodynamically insignificant or measured inaccurately. The specificity is relatively high since the stenosis in each case is relatively low.

Based on the measurement results of diameter reduction larger than 50%, the inter-rater reliability and intra-rater reliability on the stenosis are measured using Cohen's kappa coefficient, which are 0.74 and 0.45, respectively. The results indicated that the same reading has substantial agreement while the different readings have moderate agreement.

For subjects with an intermediate pre-test probability of CHD of 50% or higher, the DS measurements are compared with measurements on CCA images. The DS measurements on the each observer's most favourite image option are used. The measurement of each true positive is normalized using the corresponding CCA readings and worked as the accuracy of this measurement. The average accuracy and standard variances are calculated to assess the accuracy and overall performance of quantifying stenosis using the panoramic visualization. The DS measurements on true positives are normalized using the CCA readings and the average accuracy is 0.89±0.11. The DS measurements on each of the three image options are compared using the Wilcoxon signed-rank test and the test results are shown in Table 1 below.

TABLE 1

| First Image Option | Accuracy of First Image Option | Second Image Option | Accuracy of Second Image Option | P-Value |
|---|---|---|---|---|
| I1 | 0.853 | I2 | 0.835 | 0.21 |
| I1 | 0.853 | I3 | 0.788 | 0.03 |
| I2 | 0.835 | I3 | 0.788 | 0.10 |

A P-value of 0.05 is assumed to indicate statistical significance. The accuracy based on the original density image (image option I1) is higher than that based on the edge map (image option I3). The increase from 0.788 (of image option I3) to 0.853 (of image option I1) is statistical significant with a p-value of 0.03 (≤0.05). The accuracy increments of enhanced density image (image option I2) versus original density image (image option I1), and enhanced density image (image option I2) versus edge map (image option I3) are statistically insignificant.

Therefore, in stenosis detection, when supported by the panoramic visualization of the coronary arterial tree, experienced radiologists obtained a sensitivity of 82% and a specificity of 95%. They are able to achieve good reproducibility with Cohen's kappa coefficient of 0.74 for the intra-rater reliability and 0.45 for the inter-rater reliability. In stenosis quantification, the accuracy obtained is 0.89±0.11.

The diagnostic accuracy of the panoramic visualization for the detection and quantification of the coronary artery stenosis is thus compared with CCA images with quantitative analysis as the reference standard. The panoramic visualization results in a high true positive rate in the stenosis detection, and a high accuracy in stenosis quantification. Among the three image options, the original density image option achieves the optimum performance. In addition, the performance results from the combination of the three image options are superior to performance from any single image options. The panoramic visualization can be helpful to assist radiologists in identifying the location of the greatest narrowing.

In comparison with CCA, CTA is a minimally invasive screening tool that performs more rapidly, at less expense, and with reduced radiation dose. Regions of interest (ROI) and projection angles may be retrospectively selected to optimally demonstrate anatomical features of subjects. In embodiments of the present disclosure, the automated method 100 is able to generate a panoramic visualization of the coronary arterial tree and its efficiency is assessed. The panoramic visualization results in a high true positive rate of 82% in the stenosis detection and a high accuracy of 89% in stenosis quantification. In terms of the intra-rater reliability or agreement, the Cohen's kappa coefficient of 0.74 indicates good reproducibility.

Embodiments of the present disclosure describe an automated method 100 and system for generating a panoramic visualization of a coronary arterial tree. One potential application of the panoramic visualization is to detect and quantify the stenosis of coronary arteries. As the high-contrast MIP images in the panoramic visualization are directly comparable to CCA images, quantitative analysis of the coronary anatomy can be improved by using the panoramic visualization. MIP relies on basic radiographic biophysical properties, is robust, and has little variation (i.e. is more uniform) among vendors. This increases the confidence with which the output panoramic visualization can be analyzed and reported. The panoramic visualization also allows the 3D relationships between vessels in the coronary arterial tree to be appreciated more readily.

Adopting the use of the panoramic visualization of the coronary arterial tree can potentially change clinical routines. It enhances the efficiency and reproducibility of quantitative assessment of coronary artery stenosis. Moreover, no operator input is required to generate the requisite views. From the CTA image volume, the method 100 automatically generates multiple MIP images of usual projection views that covers all coronary segments. A radiologist reads and visually quantifies coronary stenosis in each segment of the coronary arterial tree similar to the way invasive CCA is read. There is a reduced need for performing MPR. If required, such as for borderline significant stenosis and/or research application, quantitative coronary analysis techniques used in invasive CCA readings can be adapted without modification.

In the foregoing detailed description, embodiments of the present disclosure in relation to an automated method and system for generating a panoramic visualization of a coronary arterial tree of a subject are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

What is claimed is:

1. An automated method for generating a panoramic visualization of a coronary arterial tree of a subject, the method comprising:
   acquiring an image volume of a thoracic cavity of the subject, the image volume providing a three-dimensional (3D) representation of the thoracic cavity;
   isolating a coronary structure in the 3D representation by abating one or more other anatomical structures in the thoracic cavity, the isolated coronary structure including a heart, aorta, great vessels, and the coronary arterial tree;
   abating one or more portions of the isolated coronary structure that attenuate visualization of the coronary arterial tree, the one or more portions being segmented from the aorta and coronary arterial tree;
   generating, by maximum intensity projection (MIP), a plurality of MIP images of the isolated coronary structure; and
   compositing the MIP images to generate the panoramic visualization of the coronary arterial tree
   wherein said isolating of the coronary structure comprises:
     abating the one or more other anatomical structures based on a predefined threshold value;
     generating a heart mask after abating the one or more anatomical structures; and
     extracting the coronary structure by applying a mean-shift-based technique on the heart mask.

2. The method according to claim 1, further comprising enhancing the MIP images by histogram equalization.

3. The method according to claim 1, further comprising displaying the composited MIP images in cine loop for panoramic visualization of the coronary arterial tree.

4. The method according to claim 1, wherein abating the one or more portions of the coronary structure comprises segmenting each portion from the coronary arterial tree with a separation disc.

5. The method according to claim 4, wherein abating the one or more portions of the coronary structure further comprises flood filling each portion with a seed point.

6. The method according to claim 4, wherein the one or more portions comprises a left ventricle chamber.

7. The method according to claim 1, wherein the MIP images capture multiple views of the 3D representation.

8. The method according to claim 7, wherein the 3D representation is rotatable in order to capture the multiple views thereof in the MIP images.

9. The method according to claim 1, wherein said isolating of the coronary structure further comprises:
   abating vessel-like structural elements from the heart mask; and
   dilating the heart mask affected by said abating of the vessel-like structural elements to restore a size of the heart mask.

10. A system for generating a panoramic visualization of a coronary arterial tree of a subject, the system comprising a processor configured for performing operations comprising:
   acquiring an image volume of a thoracic cavity of the subject, the image volume providing a three-dimensional (3D) representation of the thoracic cavity;
   isolating a coronary structure in the 3D representation by abating one or more other anatomical structures in the thoracic cavity, the isolated coronary structure including a heart, aorta, great vessels, and the coronary arterial tree;

abating one or more portions of the isolated coronary structure that attenuate visualization of the coronary arterial tree, the one or more portions being segmented from the aorta and coronary arterial tree;

generating, by maximum intensity projection (MIP), a plurality of MIP images of the isolated coronary structure; and compositing the MIP images to generate the panoramic visualization of the coronary arterial tree wherein said isolating of the coronary structure comprises:

abating the one or more other anatomical structures based on a predefined threshold value;

generating a heart mask after abating the one or more anatomical structures; and extracting the coronary structure by applying a mean-shift-based technique on the heart mask.

11. The system according to claim 10, the operations further comprising enhancing the MIP images by histogram equalization.

12. The system according to claim 10, the operations further comprising displaying the composited MIP images in cine loop for panoramic visualization of the coronary arterial tree.

13. The system according to claim 10, wherein abating the one or more portions of the coronary structure comprises segmenting each portion from the coronary arterial tree with a separation disc.

14. The system according to claim 13, wherein abating the one or more portions of the coronary structure further comprises flood filling each portion with a seed point.

15. The system according to claim 13, wherein the one or more portions comprises a left ventricle chamber.

16. The system according to claim 10, wherein the MIP images capture multiple views of the 3D representation.

17. The system according to claim 16, wherein the 3D representation is rotatable in order to capture the multiple views thereof in the MIP images.

18. The system according to claim 10, wherein said isolating of the coronary structure further comprises:

abating vessel-like structural elements from the heart mask; and dilating the heart mask affected by said abating of the vessel-like structural elements to restore a size of the heart mask.

\* \* \* \* \*